US010677532B2

(12) United States Patent
Kalb

(10) Patent No.: US 10,677,532 B2
(45) Date of Patent: Jun. 9, 2020

(54) IONIC LIQUIDS FOR COOLING IN HIGH TEMPERATURE ENVIRONMENT

(71) Applicant: VTU HOLDING GMBH, Grambach (AT)

(72) Inventor: Roland Kalb, Sinabelkirchen (AT)

(73) Assignee: PROIONIC GMBH, Grambach (AT)

( * ) Notice: Subject to any disclaimer, the term of this patent is extended or adjusted under 35 U.S.C. 154(b) by 0 days.

(21) Appl. No.: 14/991,674

(22) Filed: Jan. 8, 2016

(65) Prior Publication Data
US 2016/0138876 A1 May 19, 2016

Related U.S. Application Data

(62) Division of application No. 14/375,117, filed as application No. PCT/EP2012/077010 on Dec. 28, 2012, now abandoned.

(30) Foreign Application Priority Data

Feb. 2, 2012 (EP) .................... 12153670

(51) Int. Cl.
C09K 5/04 (2006.01)
F28D 15/00 (2006.01)
C09K 5/10 (2006.01)
C09K 5/06 (2006.01)
C07D 233/58 (2006.01)

(52) U.S. Cl.
CPC ........... *F28D 15/00* (2013.01); *C07D 233/58* (2013.01); *C09K 5/048* (2013.01); *C09K 5/066* (2013.01); *C09K 5/10* (2013.01)

(58) Field of Classification Search
CPC ............ F28D 15/00; C09K 5/04; C09K 5/048
USPC .................................. 252/71, 72, 73, 74, 75
See application file for complete search history.

(56) References Cited

U.S. PATENT DOCUMENTS

| 8,835,649 | B2 * | 9/2014 | Kalb ................... C07C 49/12 548/335.1 |
| 9,920,272 | B2 * | 3/2018 | Kondo .................... G11B 5/725 |
| 2005/0070717 | A1 | 3/2005 | Wasserscheid et al. |
| 2006/0251961 | A1 | 11/2006 | Olbert et al. |
| 2007/0144186 | A1 * | 6/2007 | Shiflett ................. C09K 5/047 62/112 |
| 2009/0071155 | A1 * | 3/2009 | Boyapati .................. F01K 7/36 60/649 |
| 2009/0314460 | A1 | 12/2009 | Sommerhofer et al. |
| 2010/0132384 | A1 | 6/2010 | Shiflett et al. |
| 2011/0039467 | A1 | 2/2011 | Xu |
| 2012/0138271 | A1 * | 6/2012 | Filzwieser ................ F27B 3/24 165/104.19 |
| 2013/0219949 | A1 * | 8/2013 | Seiler .................... F25B 15/00 62/476 |
| 2014/0007963 | A1 | 1/2014 | Revink et al. |
| 2019/0040767 | A1 * | 2/2019 | Kontomaris ........... C09K 5/048 |

FOREIGN PATENT DOCUMENTS

| CN | 1263924 A | 8/2000 | |
| DE | 10316418 | 10/2004 | |
| DE | 102004046042 | 9/2005 | |
| DE | 102007006455 | 8/2008 | |
| DE | 102009051087 | 5/2010 | |
| JP | 2008019505 | 1/2008 | |
| KZ | 24010 A1 | 5/2011 | |
| WO | WO2010136403 | 12/2010 | |
| WO | WO 2010136403 A1 * | 12/2010 | ............... F27B 3/24 |

OTHER PUBLICATIONS

Moens et al. "Advanced Thermal Storage Fluids for Solar Parabolic Trough Systems", Proceedings of SED2002 (2002 International Solar Energy Conference), Jun. 15-20, 2002, p. 1-7.*
Bai et al., "Applications of ionic liquids in heat transfer and heat storage process", CIESC Journal, (Chinese Edition) Dec. 2010, vol. 61, No. 12, 3037-3043.
Franca et al., "Influence of Thermophysical Properties of Ionic Liquids in Chemical Process Design", Journal of Chemical & Engineering Data (2009), 54(9), 2569-2575.
International Preliminary Report on Patentability for PCT Application Serial No. PCT/EP2012/077010 dated Aug. 5, 2014 (6 pgs).
Nieto et al; "Studies on the density, heat capacity, surface tension and infinite dilution diffusion with liquids . . .", Fluid Phase Equilibria (2010), 294(1-2), 157-179.
Roger et al.; "Ionic Liquids—Industrial Applications to Green Chemistry", ACS Symposium Series 818, 2002; ISBN 0841237891.
Van Valkenburg et al.; "Ionic Liquids As Thermal Fluids", Proceedings—Electrochemical Society (2002), 2002-19(Molten Salts XIII), 112-123.
Van Valkenburg et al: "Thermochemistry of ionic liquid heat-transfer fluids", Thermochimica Acta, Elsevier Science Publishers, Amsterdam, NL, vol. 425, No. 1-2, Jan. 20, 2005 (Jan. 20, 2005), pp. 181-188, XP027864303.
Wasserscheid et al.; "Ionic Liquids in Synthesis", Wiley-VCH 2008; ISBN 978-3-527-31239-9).
Zhang et al.; "Application of [C4min][Tf2N] Ionic Liquid as Thermal Storage and Heat Transfer Fluids", ECS Transactions (2007), 2(28, Energy Systems for the Twenty-First Century: Opportunities for Application of Solar, and Conversion Technologies), 27-34.

(Continued)

Primary Examiner — Jane L Stanley
(74) Attorney, Agent, or Firm — Workman Nydegger

(57) ABSTRACT

Cooling medium comprising an ionic liquid with a hydrogen content of 0% to 8.5% by weight. The cooling medium can be used in a method for cooling a technical device, examples of which include: metallurgical ovens and their aggregates, ovens and aggregates in the glass and ceramic producing industry, ovens and aggregates in the cement producing industry, reactors and aggregates in gasification of organic matter and biofeedstocks, ovens and aggregates in incineration plants, reactors and aggregates in nuclear power plants, and combustion chambers and aggregates in conventional thermal power plants.

20 Claims, No Drawings

(56) References Cited

OTHER PUBLICATIONS

Zhang et al.; "Mineral Processing and Extractive Metallurgy", Transactions of the Institutions of Mining and Metallurgy, Section C: Mineral Processing and Extractive Metallurgy (2010), 119(2), 71-76.

U.S. Appl. No. 14/375,117, filed Jul. 28, 2014, Office Action dated Jun. 18, 2015.

U.S. Appl. No. 14/375,117, filed Jul. 28, 2014, Final Office Action dated Oct. 8, 2015.

\* cited by examiner

IONIC LIQUIDS FOR COOLING IN HIGH TEMPERATURE ENVIRONMENT

CROSS REFERENCE TO RELATED APPLICATION

This application is a division of U.S. patent application Ser. No. 14/375,117, filed Jul. 28, 2014, the disclosure of which is incorporated herein in its entirety.

BACKGROUND

The present invention relates to ionic liquids which are useful for cooling in high temperature environment.

According to generally accepted literature an ionic liquid is a salt in the liquid state, more particularly a melt of a low melting salt, e.g. with a melting point equal or below 100° C. (see e.g. Wasserscheid, Peter; Welton, Tom (Eds.); "Ionic Liquids in Synthesis", Wiley-VCH 2008; ISBN 978-3-527-31239-9). However, it is to note that the melting temperature of ≤100° C. is chosen arbitrarily.

Such ionic liquids may exhibit some very interesting characteristics, e.g. having a very low, virtually non measurable vapor pressure, a large liquidus range, good electrical conductivity and interesting solvation characteristics. These characteristics make ionic liquids prone for several applications, e.g. as solvents (for example, in organic or inorganic synthesis, transition metal catalysis, biocatalysis, multiphase reactions, photochemistry, polymer synthesis, and nanotechnology), extracting agent (e.g. liquid-liquid or liquid gaseous extraction, sulphur removal during crude oil processing, removal of heavy metals during water processing and liquid membrane extraction), electrolytes (for example, in batteries, fuel cells, capacitors, solar cells, sensors, electroplating, electrochemical metal processing, electrochemical synthesis, and nanotechnology), lubricants, gels, reagents for organic synthesis, in the so-called "green chemistry" (e.g. as replacement for volatile organic compounds), antistatic addtives, specific applications in chemical analysis (e.g. gas chromatography, mass spectroscopy, capillary zone electrophoresis), liquid crystals, for storing and releasing hydrogen, as thermofluids, e.g. as cooling medium, etc..

In US 2009/314460 a process for strip casting is described using a travelling mould which is cooled by a liquid coolant, wherein the coolant is liquid metal or ionic liquid wherein ionic liquids are defined as a group of salts composed of organic cations and mostly inorganic anions which generally have a melting point below 100° C.

In WO 2010/136403 ionic liquids for use as a cooling medium are disclosed. It is described that ionic liquids are exclusively composed from ions (cations and anions) and are salts that are liquid at temperatures below 100° C. without the salts being dissolved in a solvent such as water. Cations according to WO 2010/136403 include imidazolium, pyridinium, pyrrolidinium, guanidinium, uronium, thiouronium, piperidinium, morpholinium, phosphonium or ammonium, which cations additionally can be alkylated and anions include sulfates, phosphates, halides, fluorinated anions such as tetrafluoroborate, hexafluoroborate, trifluoroacetate, trifluoromethanesulfonate and hexafluorophosphate, sulfonates, phosphinates or tosylates.

It is known that ionic liquids do have virtually no vapor pressure and are therefore generally non flammable below their high thermal decomposition point of up to 300° C. and even more. When heated up above their thermal decomposition temperature, however, they form gaseous, molecular decomposition products, which are flammable. In combustion experiments it can be seen, that a typical ionic liquid starts to burn after the bulk phase has reached the flashpoint temperature and that in many cases the combustion only continues, if a quite high input of external heat from a heat source is given. This is in contrast to conventional, molecular liquids: E.g. mineral oil can be ignited at temperatures of approx. 80 to 100° C., which is far below its thermal decomposition point, because mineral oil does have a vapor pressure and forms a flammable gas phase at this temperatures. As described in WO2010136403A1, ionic liquids do not form a highly explosive mixture of hydrogen and oxygen (detonating gas or oxyhydrogen gas) when in contact with hot (reducing) surfaces or hot (reducing) melts at temperatures above approx. 500° C. That is in contrast to water, which still is widely used as cooling agent. Drawbacks of ionic liquids in contrast to water may be the higher viscosity in the range of typically some 10 to some 100 mPas at 20° C. and a specific heat capacity of approx. 50 to 75% of water.

In summary, ionic liquid cooling media generally are superior to water or thermo oils as cooling agents in terms of safety. However, if ionic liquids are heated above their thermal decomposition point, they still form flammable or non flammable gaseous products, which will lead to an increase or even hazardous increase of pressure in a closed cooling system. In the case of an accidental efflux by e.g. disruption of a pipe into e.g. a molten metal it will cause heavy sputtering or even minor explosions.

SUMMARY

It is a task of the present invention to reduce or even overcome the formation of gaseous decomposition products in ionic liquid cooling media to prevent the drawbacks described above.

DETAILED DESCRIPTION

According to the present invention it was found unexpectedly, that cooling media comprising ionic liquids with 8.5 weight % of hydrogen or less, show much lower, or even practically no sputtering or explosive reaction behavior in contrast to ionic liquids (and other cooling media) with higher hydrogen content. The term "hydrogen" denotes hydrogen atoms bound to other atoms e.g. carbon atoms, being part of the ionic liquids anions or cations or being part of ionic or molecular byproducts or additives, but not gaseous hydrogen. The content of carbon atoms or other atoms forming volatile combustion products like sulfur, nitrogen, fluorine or chlorine seems to be of less importance as was found by experimental investigations.

In one aspect the present invention provides a cooling medium, e.g. for the application in high temperature environment, comprising an ionic liquid with a hydrogen content of 0% to 8.5%, such as 0% to 7% by weight, e.g. 0% to 6.5% by weight.

A cooling medium provided by the present invention is herein also designated as "cooling medium of (according to) the present invention". A cooling medium comprising an ionic liquid may be a cooling medium consisting of an ionic liquid. An ionic liquid provided by the present invention as a cooling medium is herein also designated as "ionic liquid of (according to) the present invention".

The term "ionic liquid" as used herein, e.g. in a process of the present invention, includes salts with melting temperatures of up to 250° C., e.g. ≤100° C. and >100° C., but ≤250° C.; preferably ≤100° C. and more preferably less than room temperature.

The term "ionic liquid" as used herein, further includes all liquid organic salts and mixtures of salts consisting of inorganic cations and organic anions or inorganic anions. Moreover additional salts with inorganic cation and organic or inorganic anion can be dissolved in the ionic liquid, containing but definitely not limited to the identical anion or identical anions as found in the basic ionic liquid. Moreover, additives may be dissolved in the ionic liquid, e.g. small amounts thereof, such as flame retardants.

In a further aspect the present invention provides a cooling medium according to the present invention, further comprising dissolved salts with inorganic cations and organic or inorganic anions, and/or dissolved flame retardants.

The chemical nature of cations and anions which form the ionic liquid in a cooling medium according to the present invention is less important. Appropriate cations and anions are such which form ionic liquids having a hydrogen content of not more than 8.5%, e.g. 0% to 8.5%.

In the following the term "moieties" denote alkyl, perfluorated alkyl, alkenyl, alkinyl, aryl, aralkyl or heteroaryl groups having 1 to 8 carbon atoms, such as C1-C4-alkyl, C2-C4-alkenyl, C2-C4-alkinyl, phenyl, benzyl or heteroaryl, preferably alkyl. For clarity reasons it should be mentioned that in this application the term C1-C4-alkyl or similar terms is an abbreviatory notation for C1-alkyl (methyl), C2-alkyl (ethyl), . . . , C4-alkyl (n-butyl, isobutyl, tert-butyl) or similar terms. In general branched chains are preferred, having found to be superior over linear chains.

In an ionic liquid according to the present invention preferably the cation is selected from imidazolium, benzimidazolium or phosphonium, optionally and preferably being substituted by C1 to C4 alkyl, e.g. including 1,3-dialkylimidazolium, 1,2,3-trialkylimidazolium, 1,3-dialkylbenzimidazolium, 1,2,3-trialkylbenzimidazolium, tetraalkylphosphonium cations, wherein preferably alkyl independently is C1 to C4 alkyl.

According to an exemplary embodiment of the present invention the cation is a quaternary ammonium, phosphonium, pyridinium, pyrrolium, piperidinium, pyrrolidinium, morpholinium, (benz)imidazolium or pyrazolium According to another exemplary embodiment of the present invention the cation is a quaternary ammonium or a quaternary phosphonium cation. According to another exemplary embodiment of the method the cation comprises one to four moieties as described above.

According to another exemplary embodiment of the present invention the cation is one out of the group consisting of pyridinium, pyrrolium, e.g. wherein one moiety is bound to the nitrogen atom and/or one to three moieties are bound to carbon atoms of the carbon ring.

According to another exemplary embodiment of the present invention the cation is one out of the group consisting of piperidinium, pyrrolidinium and morpholinium, e.g. wherein one or two moieties are bound to the nitrogen atom and/or one to three of the one to four moieties are bound to carbon atoms of the carbon ring.

According to another exemplary embodiment of the present invention the cation is one out of the group consisting of (benz)imidazolium and pyrazolium, e.g. wherein a respective one of the one to four moieties is bound to each nitrogen atom and/or one to three of the one to four moieties are bound to carbon atoms of the carbon ring. For clarity reasons it should be noted that in case of more than one nitrogen atom a first moiety may be bound to a first nitrogen atom and a second moiety may be bound to a second nitrogen atom.

According to another exemplary embodiment of the present invention the cation is preferably one out of the group consisting of tetramethylammonium, tetraethylammonium, triethylmethylammonium, tetrabutylammonium, tributylmethylammonium, 1,3-dimethylimidazolium, 1,3-diethylimidazolium, 1-butyl-3-methylimidazolium, 1,2,3-trimethylimidazolium, 1-ethyl-3-methylimidazolium, 1-ethyl-2,3-dimethylimidazolium, and 1-butyl-2,3-dimethylimidazolium, 1-propyl-3-methylimidazolium, 1-propyl-2,3-dimethylimidazolium, 1,3-dimethylbenzimidazolium, 1-butyl-3-methylbenzimidazolium, 1,2,3-trimethylbenzimidazolium, 1-ethyl-3-methylbenzimidazolium, 1-ethyl-2,3-dimethylbenzimidazolium, and 1-butyl-2,3-dimethylbenzimidazolium, 1-propyl-3-methylbenzimidazolium, 1-propyl-2,3-dimethylbenzimidazolium.

According to another exemplary embodiment of the present invention the cation is preferably one out of the group of N-Butyl-N-Methylpyrrolidinium, N-Propyl-N-Methylpyrrolidinium, N-Ethyl-N-Methylpyrrolidinium, N,N-Dimethylpyrrolidinium, N-tert.Butyl-N-Methylpyrrolidinium, N-iso-Propyl-N-Methylpyrrolidinium, N-iso-Propyl-N-Ethylpyrrolidinium, N,N-Di-iso-Propylpyrrolidinium, N-tert.Butyl-N-Ethylpyrrolidinium, N-Butyl-N-Methylmorpholinium, N-Propyl-N-Methylmorpholinium, N-Ethyl-N-Methylmorpholinium, N,N-Dimethylmorpholinium, N-tert.Butyl-N-Methylmorpholinium, N-iso-Propyl-N-Methylmorpholinium, N-iso-Propyl-N-Ethylmorpholinium, N,N-Di-iso-Propylmorpholinium, N-tert.Butyl-N-Ethylmorpholinium, N-Butyl-N-Methylpiperidinium, N-Propyl-N-Methylpiperidinium, N-Ethyl-N-Methylpiperidinium, N,N-Dimethylpiperidinium, N-tert.Butyl-N-Methylpiperidinium, N-iso-Propyl-N-Methylpiperidinium, N-iso-Propyl-N-Ethylpiperidinium, N,N-Di-iso-Propylpiperidinium, N-tert.Butyl-N-Ethylpiperidinium, Trimethyl-iso-Propylammonium, Dimethyl-di-iso-Propylammonium, Methyl-tri-iso-Propylammonium, Trimethyl-tert.-Butylammonium, Dimethyl-di-tert.-Butylammonium, Methyl-tri-tert.-Butylammonium, Trimethyl-iso-Propylphosphonium, Dimethyl-di-iso-Propylphosphonium, Methyl-tri-iso-Propylphosphonium, Trimethyl-tert.-Butylphosphonium, Dimethyl-di-tert.-Butylphosphonium, Methyl-tri-tert.-Butylphosphonium.

In another aspect the present invention provides a cooling medium according to the present invention, wherein the cation of the ionic liquid is selected from imidazolium, e.g. C1-C6 alky-imidazolium, such as 1-ethyl- or 1-buylimidazolium, wherein the imidzalolyl ring optionally is substituted by alkyl, e.g. C1-C4 alkyl, such as methyl.

In another aspect the present invention provides a cooling medium according to the present invention, wherein the cation of the ionic liquid is selected from imidazolium, benzimidazolium or phosphonium, optionally independently substituted by C1 to C4 alkyl, perfluoro C1 to C4 alkyl and/or by cyano, e.g. one or more cyano groups.

Anions in a ionic liquid according to the present invention include anions common in ionic liquid chemistry. Preferably the chemical formula of the anion contains 3 or less hydrogen atoms, more preferably the anions are completely hydrogen free. Preferably the anions comprise hetero elements, such as halogen, O, N, S, Si, B, P, a metallic element, such as Fe, Sb, Sn, Cu, Mo, Al, Zn, Co, Ni, Mn, W, V or Ti; these hetero elements may form (but are not limited to) complex anions with each other, e.g. the metallic elements listed above with halogen, $SCN^-$, $CN^-$, $N(CN)_2^-$ or O-containing ligands, or any other hydrogen-free ligand.

Appropriate anions include e.g. fluoride; chloride; bromide; thiocyanate; dicyanamide; hexafluorophosphate; sulfate; phosphate; hydrogen phosphate; dihydrogen phosphate; phosphonate $HPO_3^{2-}$, hydrogen phosphonate $H_2PO_3^-$; sulfamate $H_2N—SO_3^-$, methanesulfonate, dimethylphosphate, dimethylphosphonate, diethylphosphate, diethylphosphonate, tetrafluoroborate, trifluormethanesulfonate, trifluoracetate, bis(trifluormethylsulfonyl)imide, tris(trifluormethylsulfonyl)methide, fluorous alkyl phosphate, e.g. tris(pentafluorethyl)trifluorophosphate, methylsulfate, ethylsulfate, tetracyanoborate, carboranes, alkyl-spiroborates e.g. bis(oxalato)borate or bis(malonato)borate, tetra-substituted borate, e.g. of formula $$[BR^iR^jR^kR^l]^- \quad Va,$$

wherein $R^i$ to $R^l$, independently of each other, are fluorine or an organic, inorganic, aliphatic or perfluorinated aliphatic, aromatic, heteroaromatic or perfluorinated aromatic or heteroaromatic residues, e.g. aliphatic residues comprising 1 to 4, aromatic or heteroaromatic residues comprising 5 to 10 carbon atoms, optionally comprising one or more heteroatoms and/or optionally substituted by one or more hydrogen-free functional groups or halogen;
organic sulfonate, e.g. of formula $$[R^m—SO_3]^- \quad Vb,$$

wherein $R^m$ is an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, optionally comprising one or more heteroatoms and/or optionally substituted by one or more hydrogen-free functional groups or halogen;
organic sulfate, e.g. of formula $$[R^m—OSO_3]^- \quad Vc,$$

wherein $R^m$ is an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, optionally comprising one or more heteroatoms and/or optionally substituted by one or more hydrogen-free functional groups or halogen;
carboxylate, e.g. of formula $$[R^n—COO]^- \quad Vd,$$

wherein $R^n$ is an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, which optionally comprises one or more heteroatoms and/or optionally substituted by one or more hydrogen-free functional groups or halogen;
(fluoroalkyl)fluorophosphate e.g. of formula $$[PF_x(C_yF_{2y+1-z}H_z)_{6-x}]^- \quad Ve,$$

wherein $1 \leq x \leq 6$, $1 \leq y \leq 8$ and $0 \leq z \leq 2y+1$;
imide of formulae $$[R^o—SO_2—N—SO_2—R^p]^- \quad Vf,$$

$$[R^r—SO_2—N—CO—R^s]^- \quad Vg, or$$

$$[R^t—CO—N—CO—R^u]^- \quad Vh,$$

wherein $R^o$ to $R^u$ independently of each other are fluorine or an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, which optionally comprises one or more heteroatoms and/or optionally is substituted by one or more hydrogen-free functional groups or halogen;
organic phosphate of formula $$[R^m—OPO_3]^{2-} \text{ or}(Vj)[R^m—OPO_2—OR^n]^- \quad Vi,$$

wherein $R^m$ is an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, which optionally comprises one or more heteroatoms and/or which optionally is substituted by one or more hydrogen-free functional groups or halogen; and wherein $R^n$ is hydrogen or an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, which optionally comprises one or more heteroatoms and/or optionally substituted by one or more hydrogen free functional groups or halogen;
organic phosphonate of formula $$[R^m—PO_3]^{2-} \quad Vk, or$$

$$[R^m—PO_3—R^n]^- \quad Vl,$$

wherein $R^m$ is an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, which optionally comprises one or more heteroatoms and/or optionally is substituted by one or more hydrogen free functional groups or halogen;
and wherein $R^n$ is hydrogen or an organic, inorganic, aliphatic or perfluorinated aliphatic, aromatic, heteroaromatic or perfluorinated aromatic or heteroaromatic residue, e.g. aliphatic residues comprising 1 to 4, aromatic or heteroaromatic residues comprising 5 to 10 carbon atoms, which optionally comprises one or more heteroatoms and/or optionally substituted by one or more hydrogen-free functional groups or halogen.

In a preferred embodiment of the present invention an anion includes sulfates, phosphates, sulfonates. borates, halides, e.g. fluorides such as SiF6, tetrafluoroborates, or chlorides, e.g. tetrachloroferrat-(III), which anions optionally are alkylated, e.g. by C1-C8 alkyl, including halogenated C1-C8 alkyl, such as trifluoromethyl, or arylated, e.g. by phenyl groups, e.g. including C1-C4 alkylsulfates, such as methylsulfate, ethylsulfate, C1-C6 dialkylphosphates, such as diethylphosphate, C1-C4 alkylsulfonates wherein alkyl optionally is halogenated, e.g. fluorinated, such as methansulfonate, trifluoromethansulfonate, $SiF_6^{2-}$, halogenated, e.g. fluorinated borates, e.g. tetrafluoroborate, arylated phosphates, e.g. triphenylphosphate, ferrates, such as tetrachloroferrate-(III); e.g. diethylphosphate, triphenylphosphate, methansulfonate, trifluormethansulfonate, methylsulfate, ethylsulfate, $SiF_6^{2-}$, tetrachloroferrat-(III) and/or tetrafluoroborate.

Ionic liquids according to the present invention may be prepared as appropriate, e.g. according, e.g. analogously to a known method, e.g. as described in prior art. Processes for the preparation of ionic liquids are known e.g. from Wasserscheid, Peter; Welton, Tom (Eds.); "Ionic Liquids in Synthesis", Wiley-VCH 2008; ISBN 978-3-527-31239-9; Rogers, Robin D.; Seddon, Kenneth R. (Eds.); "Ionic Liquids—Industrial Applications to Green Chemistry", ACS Symposium Series 818, 2002; ISBN 0841237891 and numberous references cited therein.

It was found that ionic liquids according to the present invention have a high flash point. In another aspect the present invention provides a cooling medium according of the present invention wherein the ionic liquid has a flash point of at least 200° C., such as 250° C., determined according to DIN ISO 2592.

Preferably, a ionic liquid according to the present invention has a low melting point, e.g. from −20° C. and below to 40° C.

In another aspect the present invention provides a cooling medium according to the present invention, wherein the ionic liquid has a melting point from 40° C. and below, such as 20° C. and below, e.g. 0° C. and below, such as −20° C. and below.

A cooling medium of the present invention comprising ionic liquids with low hydrogen content is particularly useful in terms of safe use because of low reactivity, low flame volume and low explosiveness in a high temperature environment, especially when getting in contact with high temperature melts or surfaces.

A cooling medium of the present invention is particularly useful for the following applications:
- Cooling of technical devices in high temperature environments (500° C.-2000° C.) as a replacement of water or water-based cooling fluids or as a replacement of cooling fluids based on organic liquids—so called thermo oils—e.g. paraffins and naphthens, mineral oils, alkyl-benzenes, benzyl- and dibenzyltoluenes, biphenyls, diphenylethers, terphenyls, partially hydrogenated terphenyls, quaterphenyles, triarylethers, alkylnaphthalines, polyalkylenglykoles, high boiling esters, silicon oils, in order to prevent the formation of explosive decomposition reactions with destructive or even devastating consequences in the case of technical failures, human error, natural disasters and accidents.
- In particular cooling of metallurgical ovens and their aggregates; cooling of metallurgical equipment in general in production and processing of metals, metal alloys and intermetalic compounds, handling of ashes and slags, including production and processing of silicon, refractory metals and intermetalic compounds with boron, carbon, nitrogen and silicon. Fused-salt electrolysis for the production of e.g. aluminum or sodium.
- Cooling of ovens and aggregates in the glas and ceramic producing industry
- Cooling of ovens and aggregates in the cement producing industry
- Cooling of reactors and aggregates in gasification of organic matter and biofeedstocks.
- Cooling of ovens and aggregates in incineration plants, including waste gas incineration e.g. by afterburners and cooling of ashes and slags
- Cooling of reactors and aggregates in nuclear power plants
- Cooling of combustion chambers and aggregates in conventional thermal power plants.

In another aspect the prent invention provides the use of a cooling medium according to the present invention for the cooling of
- technical devices in high temperature environment,
- metallurgical ovens and their aggregates,
- ovens and aggregates in the glas and ceramic producing industry,
- ovens and aggregates in the cement producing industry,
- cooling of reactors and aggregates in gasification of organic matter and biofeedstocks,
- ovens and aggregates in incineration plants,
- reactors and aggregates in nuclear power plants,
- combustion chambers and aggregates in conventional thermal power plants.

Example 1

5 kg of molten copper was kept in a small metallurgical oven at constant temperature at 1200° C. All professional precautions known to an expert in the field of metallurgy where taken into account, e.g. fume hood, fireproof safety clothing and helmet, fireproof curtains etc. The ionic liquid test fluids where pumped with a constant flow of 1 ml/s through a ¼" stainless steel capillary right into the copper melt. The steel capillaries outlet was immersed into the molten copper directly above the bottom of the crucible which is the worst position in terms of possible explosive reactions. The experiments were filmed and observed by a team of metallurgical experts. Their visual and acoustic attention was focused especially on sputtering of the copper melt, explosive reactivity and flame volume. These parameters where rated by the following numbers:

Reactivity: 0-5
0=no observable sputtering, gas evolution or explosive evaporation
5=very heavy sputtering, gas evolution or explosive evaporation
Flame volume: 0-5
0=no observable flames
5=very large flame volume
Benchmark: Mineral oil "Castrol HDX", see table
Results:

In the following Table 1 composition of ionic liquids, their sum formulae, the calculated content in weight % of carbon atoms "C", hydrogen atoms "H" and other atoms "Z" which may form gaseous combustion products, the T-Onset temperature for the decomposition in air measured by a thermo balance (according to DIN 51007), the flashpoint (according to DIN ISO 2592) and the ratings for the reactivity (RA) and the flame volume (FV). The individual weight % s listed are based on the total mol weight of the composition. Z=other atoms forming gaseous combustion products, e.g. N, S, F, Cl, but except O. EMIM is 1-Ethyl-3-methylimidazolium and BMIM is 1-Butyl-3-methylimidazolium.

TABLE 1

| Composition | Sum formula | C [% w] | H [% w] | Z [% w] | T-Onset | Flash point | RA | FV |
|---|---|---|---|---|---|---|---|---|
| Mineral oil "Castrol HDX" | — | — | — | — | — | — | 5 | 5 |
| BMIM-octyl sulfate | $C_{16}H_{32}N_2O_4S$ | 55.14 | 9.26 | 17.24 | 224° C. | 288° C. | 3.5 | 3.5 |
| EMIM-diethylphosphate | $C_{10}H_{21}N_2O_4P$ | 45.45 | 8.01 | 10.60 | 264° C. | 222° C. | 3 | 2 |

TABLE 1-continued

| Composition | Sum formula | C [% w] | H [% w] | Z [% w] | T-Onset | Flash point | RA | FV |
|---|---|---|---|---|---|---|---|---|
| EMIM-methansulfonate/ BMIM-methylsulfate 50:50 | $C_7H_{14}N_2O_3S$ $C_9H_{18}N_2O_4SC$ | 41.97 | 7.05 | 26.57 | — | — | 2 | 1.5 |
| EMIM-methansulfonate | $C_7H_{14}N_2O_3S$ | 40.76 | 6.84 | 29.13 | 339° C. | 290° C. | 2 | 2 |
| EMIM-methansulfonate/ $EMIM_2$-$SiF_6$ 90:10 | $C_7H_{14}N_2O_3S$ $C_{12}H_{22}F_6N_4Si$ | 40.64 | 6.77 | 30.88 | — | — | 2 | 2 |
| EMIM-methansulfonate/ BMIM-tetrafluoroborate 50:50 | $C_7H_{14}N_2O_3S$ $C_8H_{15}BF_4N_2$ | 41.64 | 6.77 | 37.83 | — | — | 1.5 | 2 |
| EMIM-ethylsulfate/ $EMIM_2$-$SiF_6$ 90:10 | $C_8H_{16}N_2O_4S$ $C_{12}H_{22}F_6N_4Si$ | 40.55 | 6.76 | 27.55 | 308° C. | 272° C. | 2 | 2 |
| EMIM-methansulfonate/ Triphenylphosphate 90:10 | $C_7H_{14}N_2O_3S$ $C_{18}H_{15}O_4P$ | 43.31 | 6.62 | 26.22 | — | — | 1.5 | 2 |
| EMIM-methansulfonate/ Fe-trifluormethansulfonate 92:8 | $C_7H_{14}N_2O_3S$ $C_2F_6FeO_6S_2$ | 38.04 | 6.29 | 30.83 | — | — | 1.5 | 2 |
| EMIM-methansulfonate/ EMIM-tetrafluoroborate 50:50 | $C_7H_{14}N_2O_3S$ $C_6H_{11}BF_4N_2$ | 38.58 | 6.22 | 40.84 | — | — | 1.5 | 2 |
| EMIM-Tetrafluoroborate | $C_6H_{11}BF_4N_2$ | 36.40 | 5.60 | 52.54 | — | — | 1 | 2 |
| EMIM-Trifluormethansulfonate | $C_7H_{11}F_3N_2O_3S$ | 32.31 | 4.26 | 44.98 | 405° C. | 344° C. | 1 | 2 |
| EMIM-tetrachloroferrat-(III) | $C_6H_{11}Cl_4FeN_2$ | 23.34 | 3.59 | 54.99 | 390° C. | — | 1 | 1 |

The results in Table 1 above show the results for a number of ionic liquids, which were chosen due to their quite high thermal decomposition points/flashpoints and low melting points (all are liquid at room temperature except EMIM-methansulfonate and Bmim-octylsulfate with a melting points of 34-35° C.). From Table 1 it is evident, that the reactivity RA and the flame volume FV decreases with decreasing hydrogen content, even if the content of other atoms forming gaseous combustion products increases. Moreover it can be seen that a hydrogen content of 9.26% shows a sharp distinction regarding RA and FV with compound of the present invention wherein the hydrogen content is below 8.5%. E.g. reactivity RA decreases from 3.5 of the compound with a hydrogen content from more than 8.5% (9.26%) at least to 3 (decrease of ca. 14%) down to 1 (decrease of ca. 71%) of ionic liquids of the present invention. Similarly the flame volume decreases from 3.5 of the compound with a hydrogen content from more than 8.5% (9.26%) to at least to 2 (decrease of ca. 43%) down to 1 (decrease of ca. 71%) of the ionic liquids of the present invention.

In the list below prior art regarding Ionic Liquids is listed:

Bai, Liguang; Zhu, Jiqin; Chen, Biaohua; Li, Chengyue; Fei, Weiyang; Huagong Xuebao (Chinese Edition) (2010), 61(12), 3037-3043.

Zhang, M. M.; Reddy, R. G.; Transactions of the Institutions of Mining and Metallurgy, Section C: Mineral Processing and Extractive Metallurgy (2010), 119(2), 71-76.

Nieto de Castro, Carlos A.; Langa, Elisa; Morais, Ana L.; Lopes, Manuel L. Matos; Lourenco, Maria J. V.; Santos, Fernando J. V.; Santos, M. Soledade C. S.; Lopes, Jose N. Canongia; Veiga, Helena I. M.; Macatrao, Mafalda; et al; Fluid Phase Equilibria (2010), 294(1-2), 157-179.

Szarvas, Laszlo; Gerhard, Dirk; Oehlenschlaeger, Steffen; Alemany, Aurelie; Ger. Offen. (2010), DE 102009051087 A1 20100506

Franca, Joao M. P.; Nieto de Castro, Carlos A.; Matos Lopes, Manuel; Nunes, Valentim M. B.; Journal of Chemical & Engineering Data (2009), 54(9), 2569-2575.

Zhang, Mingming; Reddy, Ramana G.; ECS Transactions (2007), 2(28, Energy Systems for the Twenty-First Century: Opportunities for Application of Solar, and Conversion Technologies), 27-34.

Van Valkenburg, Michael E.; Vaughn, Robert L.; Williams, Margaret; Wilkes, John S.; Thermochimica Acta (2005), 425(1-2), 181-188.

Olbert, Gerhard; Mattke, Torsten; Fiene, Martin; Huttenloch, Oliver; Hammon, Ulrich; Ger. Offen. (2004), DE 10316418 A1 20041021

Van Valkenburg, Michael E.; Vaughn, R. Larry; Williams, Margaret; Wilkes, John S.; Proceedings—Electrochemical Society (2002), 2002-19(Molten Salts XIII), 112-123.

The invention claimed is:

1. A method for the cooling of a technical device in a high temperature environment, comprising:
   treating the technical device with a cooling medium,
   wherein the technical device has a temperature of about 500° C. to 2000° C.,
   wherein the cooling medium consists of an ionic liquid with a hydrogen content of 0% to 8.5% by weight, and
   wherein the ionic liquid includes a cation selected from the group consisting of imidazolium, (benz)imidazolium, phosphonium, quaternary ammonium, pyridinium, pyrrolium, piperidinium, pyrrolidinium, morpholinium, and pyrazolium,
   provided that when the cation is an imidazolium, and the imidazolium is a 1-butyl-3-methylimidazolium, the ionic liquid includes an anion selected from the group consisting of a sulfate, phosphate, sulfonate, borate, sulfamate, and halide,
      wherein when the anion is a phosphate, the phosphate is selected from the group consisting of hydrogen phosphate, dihydrogen phosphate, dialkylphosphate, fluorous alkyl phosphate, and arylated phosphate,
      wherein when the anion is a borate, the borate is selected from the group consisting of alkyl-spiroborate and tetra-substituted borate, wherein each residue of the tetra-substituted borate is independently an aliphatic, perfluorinated aliphatic, aromatic, heteroaromatic, perfluorinated aromatic, or perfluorinated heteroaromatic residue, and wherein when the anion is a halide, the halide is selected from the group consisting of $SiF_6^{2-}$ and tetrachloroferrate-(III), provided that when the cation is an imidazolium, and the imidazolium is a 1-ethyl-3-methylimidazolium, the ionic liquid includes an anion selected from the group consisting of a sulfate, phosphate, sulfonate, borate, sulfamate, and halide, provided that when the cation is a phosphonium, the phosphonium is a tetraalkylphosphonium and each alkyl of the tetraalkylphosphonium is a C1 to C4 alkyl, provided that when the cation is a quaternary ammonium, the quaternary ammonium is selected from the group consisting of tetramethylammonium, tetraethylammonium, triethylmethylammonium, tetrabutylammonium, tributylmethylammonium, trimethyl-iso-propylammonium, dimethyl-di-iso-propylammonium, methyl-tri-iso-propylammonium, trimethyl-tert-butylammonium, dimethyl-di-tert-butylammonium, and methyl-tri-tert-butylammonium, provided that when the cation is a pyridinium, the ionic liquid includes an anion selected from the group consisting of a sulfate, phosphate, sulfonate, borate, sulfamate, and halide, wherein when the anion is a halide, the halide is selected from the group consisting of $SiF_6^{2-}$ and tetrachloroferrate-(III), and provided that when the cation is a pyrrolidinium, the pyrrolidinium includes two moieties bound to the nitrogen atom.

2. The method of claim 1, wherein the cooling medium consists of an ionic liquid with a hydrogen content of 0% to 7% by weight.

3. The method of claim 1, wherein the cooling medium consists of an ionic liquid with a hydrogen content of 0% to 6.5% by weight.

4. The method of claim 1, wherein the ionic liquid has a flash point of at least 200° C. determined according to DIN ISO 2592.

5. The method of claim 1, wherein the ionic liquid has a flash point of at least 250° C. determined according to DIN ISO 2592.

6. The method of claim 1, wherein the ionic liquid has a melting point of 40° C. or less.

7. The method of claim 1, wherein the ionic liquid has a melting point of −20° C. or below.

8. The method of claim 1, wherein the ionic liquid includes a cation selected from imidazolium, benzimidazolium, or phosphonium, where the cation is substituted by at least any one selected from the group consisting of C1 to C4 alkyl, perfluoro C1 to C4 alkyl and cyano.

9. The method of claim 1, wherein the ionic liquid includes an anion that comprises a hetero element.

10. The method of claim 1, wherein the ionic liquid includes an anion containing 3 hydrogen atoms or less.

11. The method of claim 1, wherein the ionic liquid includes an anion that is at least any one selected from the group consisting of diethylphosphate, triphenylphosphate, methansulfonate, trifluormethansulfonate, methylsulfate, ethylsulfate —$SiF_6^{2-}$, tetrachloroferrat-(III), and tetrafluoroborate.

12. The method of claim 1, wherein the ionic liquid includes an anion that is hydrogen free.

13. The method of claim 1, wherein when the cation is a 1-butyl-3-methylimidazolium or a 1-ethyl-3-methylimidazolium, and the anion is a sulfonate, the sulfonate is according to formula $$[R'''—SO_3]^- \qquad Vb,$$

wherein $R'''$ is an inorganic, aliphatic, perfluorinated aliphatic, aromatic, heteroaromatic, perfluorinated aromatic, or perfluorinated heteroaromatic residue, wherein when $R'''$ is a perfluorinated aliphatic residue, $R'''$ is a trifluoroacetate.

14. The method of claim 1, wherein the ionic liquid is formed from at least two different ionic liquid compounds.

15. The method of claim 1, further comprising:
applying the cooling medium to cool a technical device with a temperature of 500° C. to 2000° C., wherein the technical device is
a metallurgical oven and its aggregates,
an oven and aggregates in the glass and ceramic producing industry,
an oven and aggregates in the cement producing industry,
an oven and aggregates in an incineration plant,
a reactor and aggregates in a nuclear power plant, or
a combustion chamber and aggregates in a conventional thermal power plant,
wherein the cooling medium is contacted with a high temperature melt or surface.

16. The method of claim 15, wherein the cooling medium is contacted with the high temperature melt or surface as a result of a technical failure.

17. The method of claim 15, wherein the cooling medium comprises an ionic liquid with a hydrogen content of 0% to 7% by weight.

18. The method of claim 15, wherein the cooling medium comprises an ionic liquid with a hydrogen content of 0% to 6.5% by weight.

19. The method of claim 15, wherein the ionic liquid includes a cation selected from ammonium, phosphonium, pyridinium, pyrrolium, piperidinium, pyrrolidinium, morpholinium, (benz)imidazolium, or pyrazolium.

20. The method of claim 15, wherein the ionic liquid includes an anion containing 3 hydrogen atoms or less.

* * * * *

UNITED STATES PATENT AND TRADEMARK OFFICE
CERTIFICATE OF CORRECTION

PATENT NO. : 10,677,532 B2
APPLICATION NO. : 14/991674
DATED : June 9, 2020
INVENTOR(S) : Roland Kalb It is certified that error appears in the above-identified patent and that said Letters Patent is hereby corrected as shown below:

In the Specification

Column 2
Line 17, change "as cooling" to —as a cooling—

Column 3
Line 44, after "pyrazolium" add —.—

Column 5
Line 20, change "4, aromatic" to —4 carbon atoms, aromatic—
Line 30, change "4, aromatic" to —4 carbon atoms, aromatic—
Line 39, change "4, aromatic" to —4 carbon atoms, aromatic—
Line 49, change "4, aromatic" to —4 carbon atoms, aromatic—

Column 6
Line 1, change "4, aromatic" to —4 carbon atoms, aromatic—
Line 11, change "4, aromatic" to —4 carbon atoms, aromatic—
Line 31, change "4, aromatic" to —4 carbon atoms, aromatic—
Line 39, change "4, aromatic" to —4 carbon atoms, aromatic—
Line 45, change "sulfonates." to —sulfonates,—

Column 7
Line 10, change "a ionic" to —an ionic—
Line 48, change "glas" to —glass—

Column 8
Line 3, change "prent" to —present—
Line 8, change "glas" to —glass—

Signed and Sealed this
Eighteenth Day of August, 2020

Andrei Iancu
*Director of the United States Patent and Trademark Office*

Column 9
Lines 36-37, change "compound" to —compounds—

In the Claims

Column 11
Line 52, In the Claim 8 change "perfluoro" to —preferably—